(12) United States Patent
Balus

(10) Patent No.: US 12,714,474 B2
(45) Date of Patent: Aug. 25, 2026

(54) ROD TO ROD CONNECTOR IMPLANT

(71) Applicant: GLOBUS MEDICAL, INC., Audubon, PA (US)

(72) Inventor: Alexandru Balus, San Diego, CA (US)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 18/727,375

(22) PCT Filed: Jan. 4, 2023

(86) PCT No.: PCT/US2023/060123
§ 371 (c)(1),
(2) Date: Jul. 9, 2024

(87) PCT Pub. No.: WO2023/147207
PCT Pub. Date: Aug. 3, 2023

(65) Prior Publication Data

US 2025/0099138 A1 Mar. 27, 2025

Related U.S. Application Data

(60) Provisional application No. 63/303,469, filed on Jan. 26, 2022.

(51) Int. Cl.
*A61B 17/70* (2006.01)

(52) U.S. Cl.
CPC ........ *A61B 17/7041* (2013.01); *A61B 17/705* (2013.01)

(58) Field of Classification Search
CPC .............. A61B 17/7049; A61B 17/705; A61B 17/7052
See application file for complete search history.

(56) References Cited

U.S. PATENT DOCUMENTS

| | | | | |
|---|---|---|---|---|
| 8,771,319 B2 * | 7/2014 | Prajapati | A61B 17/7052 606/250 |
| 10,624,679 B2 * | 4/2020 | Murray | A61B 17/705 |
| 2003/0018334 A1 * | 1/2003 | Richelsoph | A61B 17/7052 606/252 |
| 2005/0080416 A1 * | 4/2005 | Ryan | A61B 17/7049 606/252 |
| 2017/0333087 A1 * | 11/2017 | Lee | A61B 17/7049 |
| 2017/0333088 A1 * | 11/2017 | Lee | A61B 17/8645 |
| 2018/0228518 A1 * | 8/2018 | Carruth | A61B 17/7001 |
| 2019/0167313 A1 * | 6/2019 | Ortiz | A61B 17/7049 |

* cited by examiner

*Primary Examiner* — Jan Christopher L Merene

(57) ABSTRACT

A rod-to-rod connector implant is disclosed herein, the rod-to-rod connector implant being configured for joining a first rod and a second rod in a spinal fixation procedure. In various embodiments, disclosed herein are the rod-to-rod connector implant; a spinal fixation system comprising such a rod-to-rod connector implant, a first rod, and a second rod to be joined or coupled to the first rod by the connector implant; a method of inserting a rod-to-rod connector implant; and a kit comprising a rod-to-rod connector implant and a pair of forceps configured for use in inserting the connector implant into a patient.

20 Claims, 9 Drawing Sheets

100
1111
1103
1109
1105
1102
1106
1107
130
110
1204
120
1205
1108
120
1203
1101
D
P 100
1106
1105
1102
1205
1204
1301
120
1203
210
1101

100
1106
D
1105
1102
1205
1204
120
1203
P
210
1101
1110
1401

100
1601
1105
1102
1204
120
130
110
1101
D
P 100
150

100
152
220
1108
150
110
210
1109

ROD TO ROD CONNECTOR IMPLANT

CROSS REFERENCE TO RELATED APPLICATIONS

The present application is U.S. National Stage entry under 35 U.S.C. 371 of international patent application PCT/US2023/60123 filed Jan. 4, 2023, which claims priority to U.S. Provisional Patent Application No. 63/303,469, filed Jan. 26, 2022.

BACKGROUND OF THE INVENTION

The invention relates generally to connector implants for use in spinal fixation procedures. More particularly, the invention relates to a rod-to-rod connector implant having a single closure mechanism, as well as a system, method of insertion, and a kit including such a rod-to-rod connector implant.

Fixation systems may be surgically inserted to achieve and/or maintain a desired spatial relationship between bones, such as between vertebrae in a patient's spine. Typical fixation systems may include a fixation element such as a rod, which may be coupled to vertebrae by bone anchors. The treatment of certain conditions may make it desirable to couple a first rod to a second rod. For example, a procedure may involve laterally or medially coupling two or more rods together, e.g., for additional strength and support, or additional length of the construct. Other procedures may involve the revision of a prior fixation procedure, and may involve extending a previously inserted construct to additional vertebral levels. This may involve, e.g., laterally or medially coupling a second rod to an existing first rod, to allow for extension of the construct in a cranial or caudal direction.

Typically, rod-to-rod connector implants used for such a coupling between rods have openings in the posterior direction to facilitate placing a rod from the top, and using a lockscrew to fix the rod in place. This loading mechanism presents challenges when adding connectors to existing constructs in revision surgeries, because the rod location is already fixed in the patient. To add fixation elements in these revision cases, oftentimes the existing construct must be partially removed, which adds to the duration of the procedure and recovery time for the patient. A need exists for a rod-to-rod connector implant that addresses these challenges.

BRIEF DESCRIPTION OF THE INVENTION

A first aspect of the disclosure provides a rod-to-rod connector implant for joining a first rod and a second rod. The implant comprises a connector body that includes a first rod channel and a second rod channel, wherein the first rod channel opens to an opposing side of the connector body from the second rod channel, and the first rod channel is laterally offset from the second rod channel. The connector body further includes a recess spanning between the first rod channel and the second rod channel through the connector body. The implant further includes a locking member movably coupled to the connector body, the locking member being located at least partially within the recess and extending into the first rod channel and the second rod channel; and a closure member for engaging a socket in the second rod channel. In a locked position, the closure member acts as a single locking mechanism for retaining the first rod in the first rod channel and the second rod in the second rod channel.

In certain embodiments, the rod-to-rod connector implant is configured to medially or laterally join or affix a second rod to a first rod. The first rod may either be new or may be part of an existing construct. Where the first rod is part of an existing construct, the rod-to-rod connector implant facilitates the joining of the second rod thereto without the need to disassemble the existing construct, allowing for revision without removal of the existing construct.

In certain embodiments, in an unlocked position, the locking member enables the first rod to be received in the first rod channel and the second rod to be received in the second rod channel. In the locked position, the closure member engages the socket to retain the second rod in the second rod channel, and a force applied by the second rod to a second rod contact surface of the locking member retains the first rod in the first rod channel. The locking member may further comprise a first rod locking surface configured to extend into the first rod channel in the locked position, to retain the first rod in the first rod channel. The locking member may still further comprise a retention feature disposed at a distal end of the second rod contact surface. The body may further comprise a shoulder disposed proximate to a bottom of the socket, the shoulder being configured to engage with the retention feature in the unlocked position.

In certain embodiments, the locking member may be pivotably coupled to the connector body. A first bore may be provided through a thickness of the connector body, passing through a portion of the recess, and a second bore may be provided through a thickness of the locking member. The first and second bores may be aligned with one another, and a connection member may be disposed within the first and second bores, such that the locking member pivots around the connection member to move or toggle between an unlocked position and the locked position.

In certain embodiments, the first rod channel is open to a bottom surface of the connector body, the second rod channel is open to a top surface of the connector body, and the first rod channel is substantially parallel to the second rod channel. The recess may further be open to the bottom surface of the connector body, and to the second rod channel at a bottom thereof.

In certain embodiments, the socket is a guide and advancement structure, and the closure member includes a locking cap. The guide and advancement structure may further be a helically wound flange feature.

In certain embodiments, the connector body, the locking member, the connection member, and the closure member each include titanium.

A second aspect of the disclosure provides a system comprising: a first rod; a second rod; and a rod-to-rod connector implant coupling the first rod to the second rod. The connector implant comprises a connector body including a first rod channel and a second rod channel, wherein the first rod channel opens to an opposing side of the connector body from the second rod channel, and wherein the first rod channel is laterally offset from the second rod channel; and a recess spanning between the first rod channel and the second rod channel through the connector body. The connector implant further comprises a locking member movably coupled to the connector body, the locking member being located at least partially within the recess and extending into the first rod channel and the second rod channel; and a closure member for engaging a socket in the second rod channel. In a locked position, the closure member acts as a single locking mechanism for retaining the first rod in the first rod channel and the second rod in the second rod channel.

In certain embodiments, the first rod may be an index rod or an extension rod, and the second rod may be an extension rod. The first rod and the second rod may each have a circular cross section, and an outer diameter that may be independently selected from that of the other rod, and that may be, in certain embodiments, about 3.5 mm to about 4.0 mm.

A third aspect of the disclosure provides a method of inserting a rod-to-rod connector implant, comprising: a) providing a rod-to-rod connector implant including: a connector body having a first rod channel and a second rod channel, wherein the first rod channel opens to an opposing side of the connector body from the second rod channel, and wherein the first rod channel is laterally offset from the second rod channel; and a recess spanning between the first rod channel and the second rod channel through the connector body; a locking member movably coupled to the connector body, the locking member being located at least partially within the recess and extending into the first rod channel and the second rod channel; and a closure member for engaging a socket in the second rod channel. The method further comprises: b) using forceps, inserting the connector body onto the first rod such that the first rod is disposed within the first rod channel, wherein the first rod is fixed in position in a patient, c) inserting the second rod into the second rod channel from the opposing side of the connector body, d) with the second rod, contacting a second rod contact surface of the locking member, and actuating movement of the locking member at least partially out of second rod channel such that first rod locking surface extends into the first rod channel, thereby retaining first rod within the first rod channel; and e) inserting a closure member within the socket to lock the rod-to-rod connector implant onto the first and the second rods, with a single locking mechanism.

In certain embodiments, step b) may further include inserting the connector body downward onto the first rod, wherein the first rod channel opens to a bottom surface of the connector body.

In certain embodiments, step c) may further include inserting the second rod downward into the second rod channel, wherein the second rod channel is open to a top surface of the connector body.

In certain embodiments, step e) may further include inserting the closure member downward into the socket, wherein the socket is disposed at the opening of the second rod channel at the top surface of the connector body.

In certain embodiments, the first rod may be an index rod or an extension rod, and the second rod may be an extension rod.

A fourth aspect of the disclosure provides a kit comprising: a rod-to-rod connector implant; and a pair of forceps configured for use inserting the rod-to-rod connector implant into a patient. The rod-to-rod connector implant includes: a connector body having a first rod channel and a second rod channel, wherein the first rod channel opens to an opposing side of the connector body from the second rod channel, and wherein the first rod channel is laterally offset from the second rod channel. The connector body further includes a recess spanning between the first rod channel and the second rod channel through the connector body; and a pair of indentations having a shape and a size configured to complement and matingly engage with a tip of the forceps. The connector implant further comprises a locking member movably coupled to the connector body, the locking member being located at least partially within the recess of the connector body and extending into the first rod channel and the second rod channel; and a closure member for engaging a socket in the second rod channel. In a locked position, the closure member acts as a single locking mechanism for retaining the first rod in the first rod channel and the second rod in the second rod channel. According to this aspect of the disclosure, the forceps have a tip with a complementary fit with the pair of indentations.

In certain embodiments, in an unlocked position, the locking member enables the first rod to be received in the first rod channel and the second rod to be received in the second rod channel, and in the locked position, the closure member engages the socket to retain the second rod in the second rod channel, and a force applied by the second rod to a second rod contact surface of the locking member retains the first rod in the first rod channel. The locking member may further comprise a first rod locking surface configured to extend into the first rod channel in the locked position, to retain the first rod in the first rod channel.

In certain embodiments, the locking member further comprises a retention feature disposed at a distal end of the second rod contact surface. The body further comprises a shoulder disposed proximate to a bottom of the socket, the shoulder being configured to engage the retention feature in the unlocked position.

In certain embodiments, the locking member is pivotably coupled to the connector body. A first bore may be provided through a thickness of the connector body, and passing through a portion of the recess, and a second bore may be provided through a thickness of the locking member and aligned with the first bore. A connection member may be disposed within the first and second bores as disclosed further herein such that the locking member pivots around the connection member to move or toggle between an unlocked position and a locked position.

In certain embodiments, the first rod channel is open to a bottom surface of the connector body, the second rod channel is open to a top surface of the connector body, and the first rod channel is substantially parallel to the second rod channel. The recess may further be open to the bottom surface of the connector body, and to the second rod channel at a bottom thereof.

In certain embodiments, the socket is a guide and advancement structure, and the closure member a locking cap. The guide and advancement structure may further be a helically wound flange feature.

In certain embodiments, the connector body, the locking member, the connection member, and the closure member each include titanium.

These and other aspects, advantages and salient features of the invention will become apparent from the following detailed description, which, when taken in conjunction with the annexed drawings, where like parts are designated by like reference characters throughout the drawings, disclose embodiments of the invention.

Figures 1, 2:
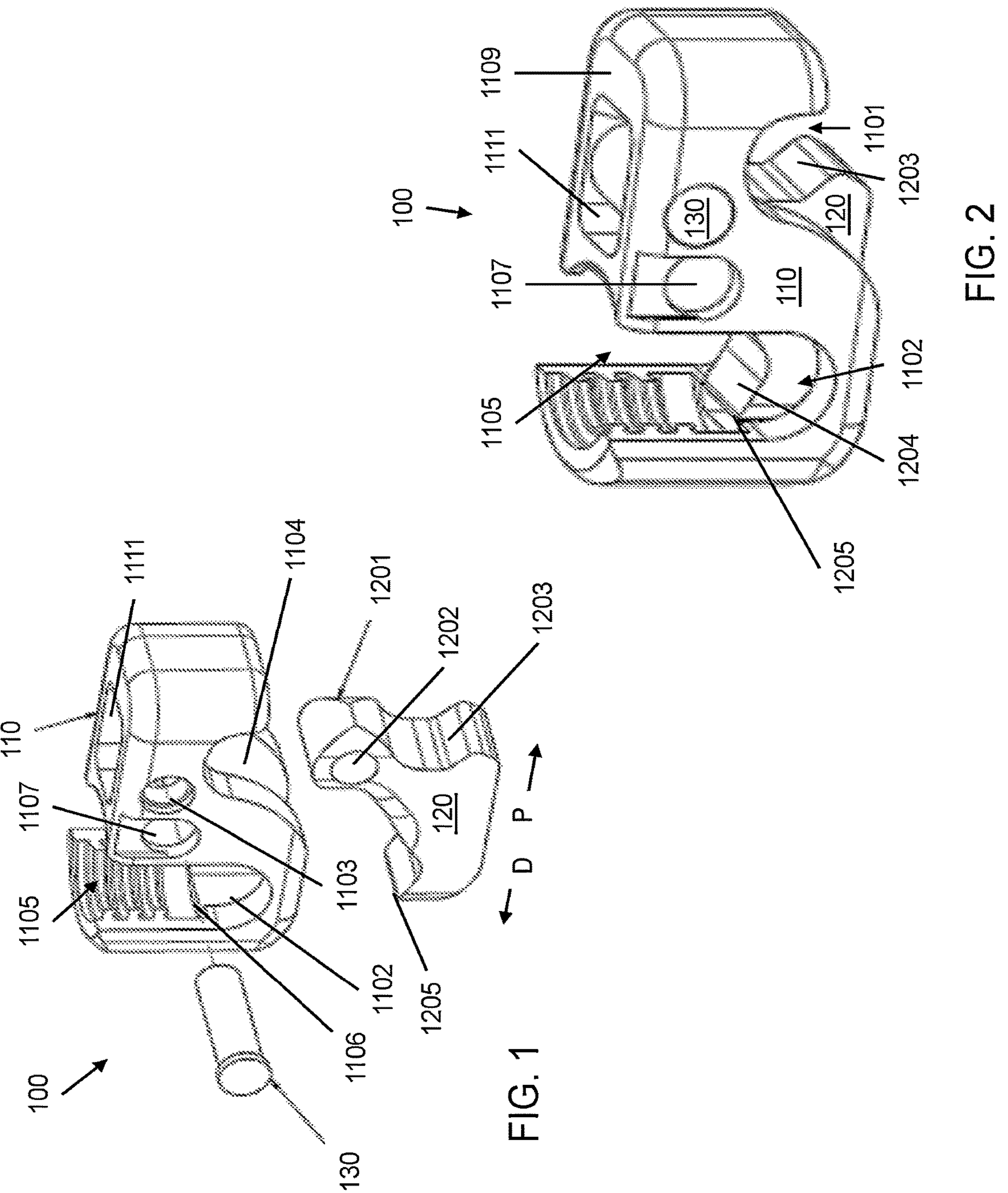
FIG. 1 shows an exploded perspective view of a rod-to-rod connector implant according to an embodiment of the invention.
FIG. 2 shows a perspective view of a rod-to-rod connector implant according to an embodiment of the invention.
Figure 3:
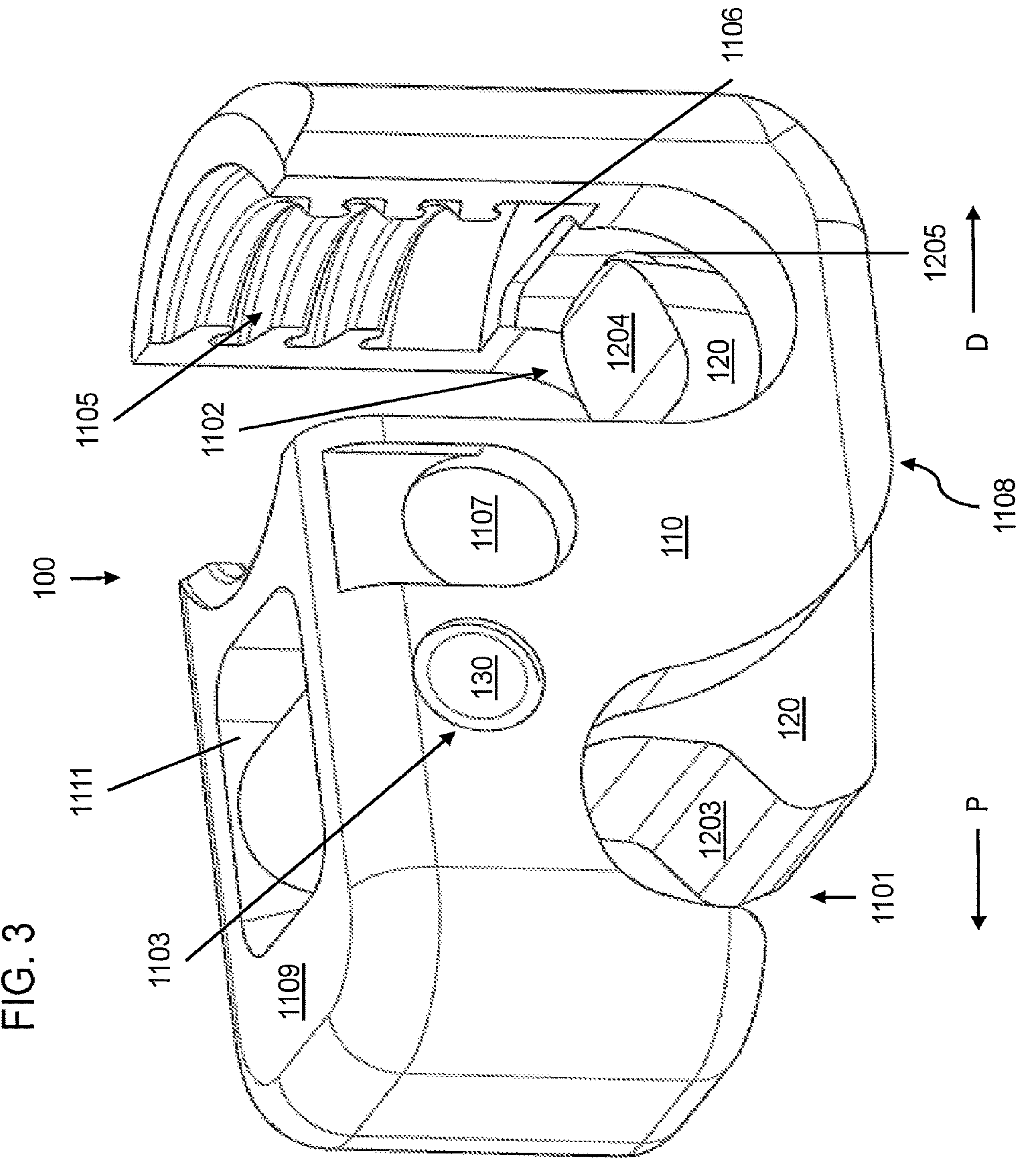
FIG. 3 shows a perspective view of a rod-to-rod connector implant according to an embodiment of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

As indicated above, aspects of the invention provide a rod-to-rod connector implant (or "connector implant") for joining a first rod and a second rod, as well as a spinal fixation system comprising such a rod-to-rod connector implant, a first rod, and a second rod to be joined or coupled to the first rod by the connector implant, a method of inserting a rod-to-rod connector implant, and a kit comprising a rod-to-rod connector implant and a pair of forceps configured for use in inserting the connector implant into a patient.

As used herein the terms proximal and distal are defined with respect to the locking member 120 (FIG. 1). The proximal direction is shown in FIG. 1 as direction P, and refers to the direction in which the locking member 120 extends toward and into first rod channel 1101. The distal direction is shown in FIG. 1 as direction D, and refers to the direction opposite the proximal direction, and the direction in which the locking member 120 extends toward and into the second rod channel 1102.

Figure 9:
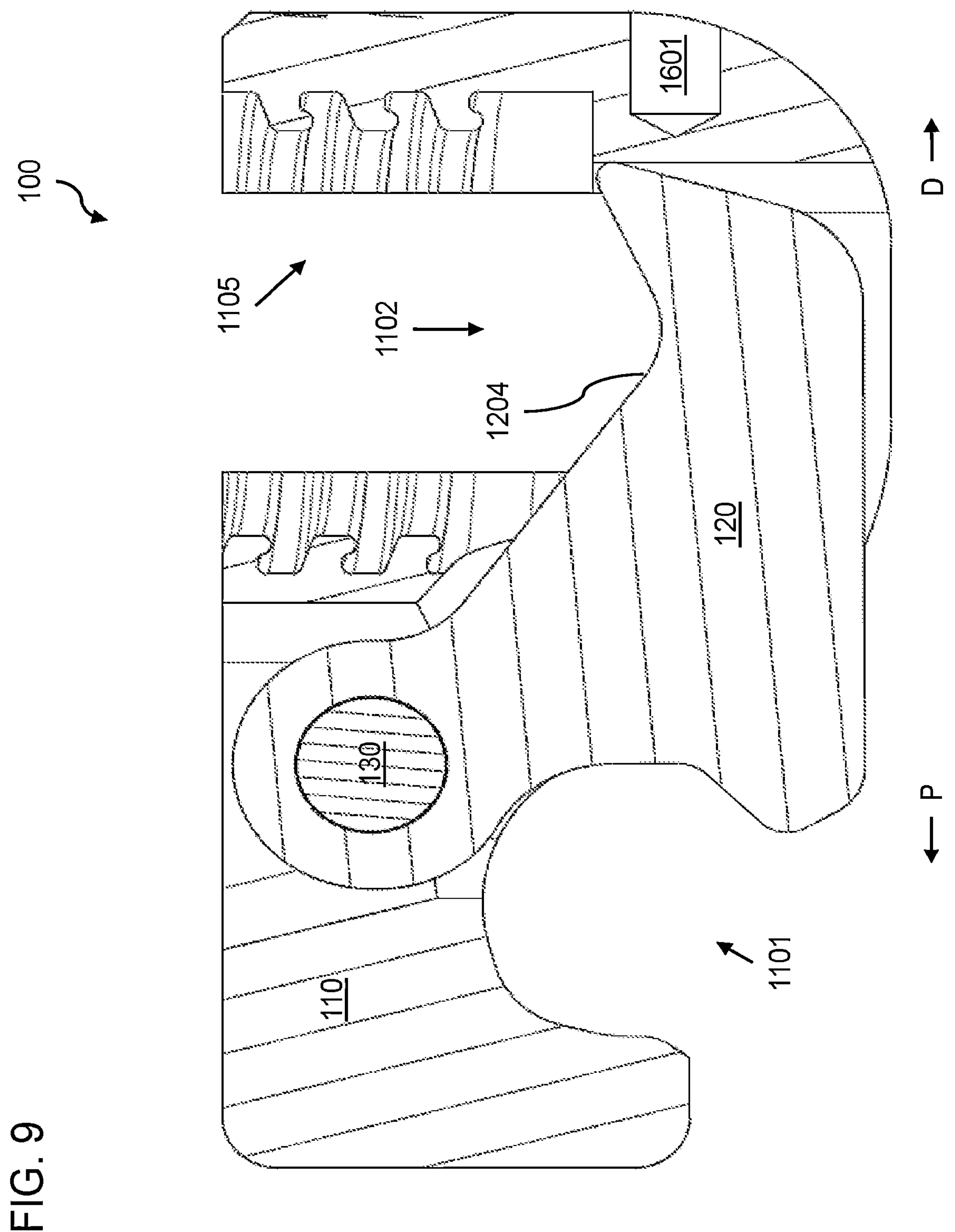
FIG. 9 shows a side cross sectional view of a portion of rod-to-rod connector implant including a locking member retention mechanism according to an embodiment of the invention.
Figure 10:
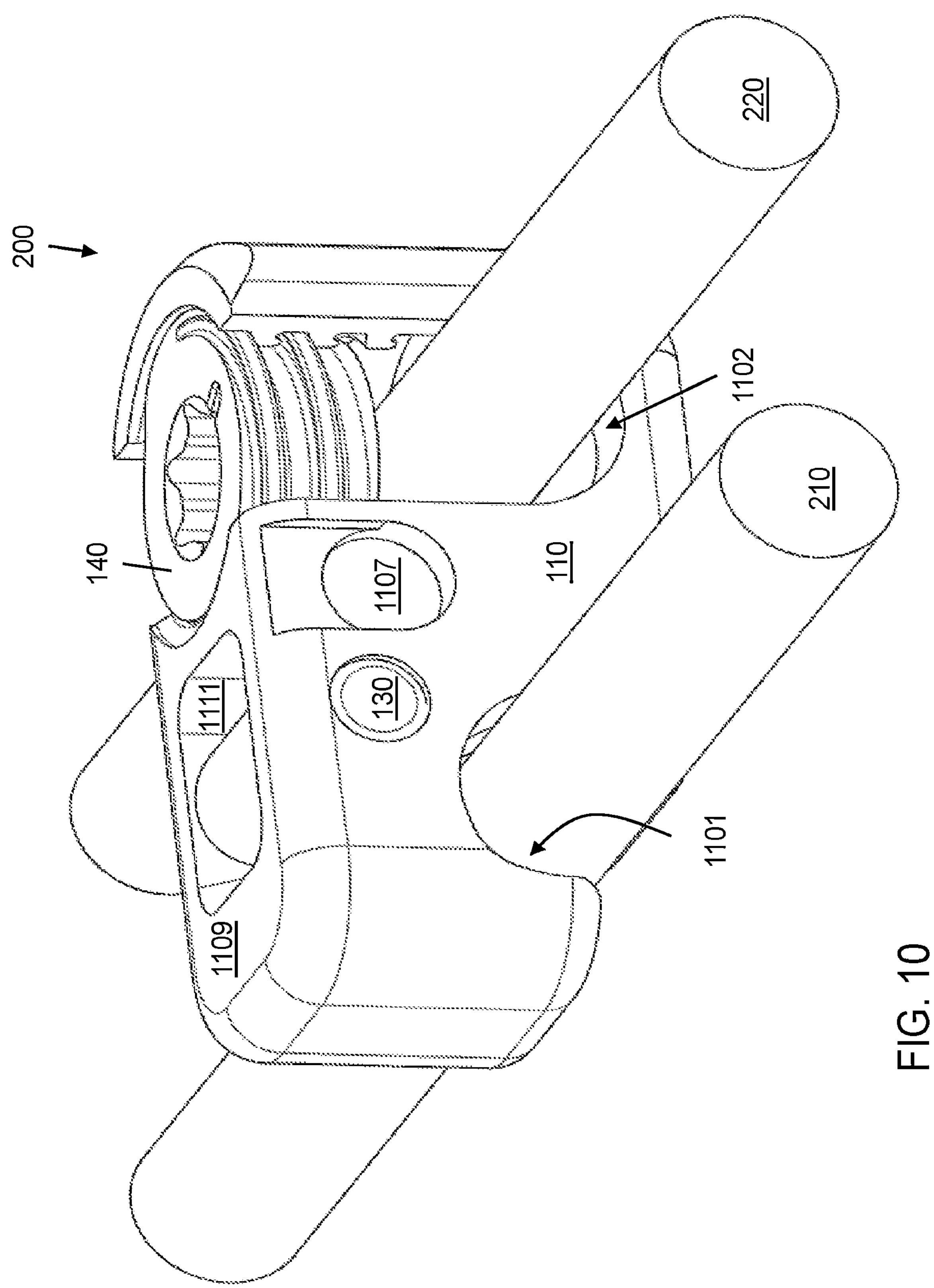
FIGS. 10 and 11 show a perspective view and a side view, respectively, of a spinal fixation system including a first rod, a second rod, and a rod-to-rod connector implant in a locked position according to an embodiment of the invention.
Figure 11:
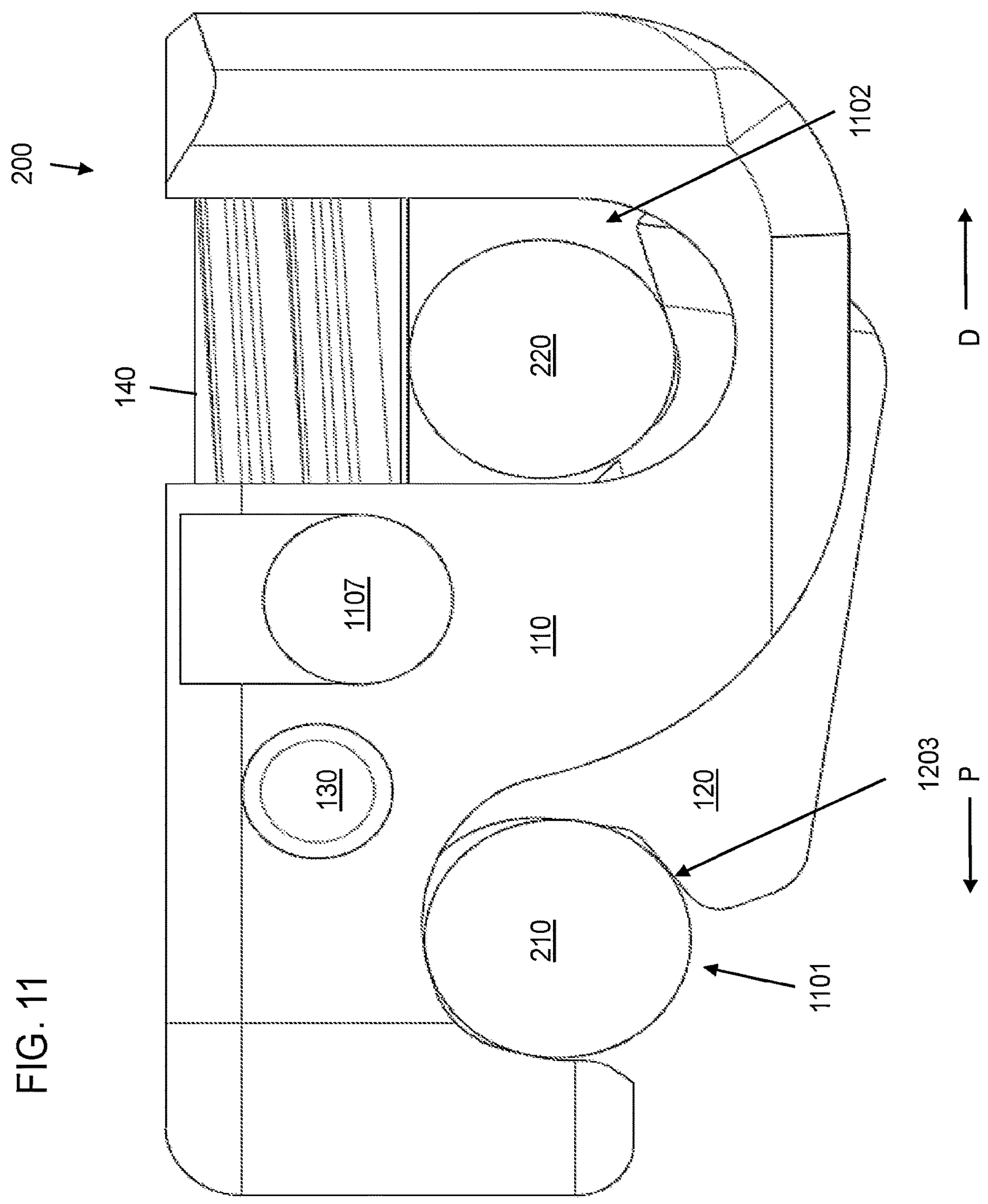

As indicated above, aspects of the invention provide a rod-to-rod connector implant 100 (FIGS. 1-9) for joining a first rod 210 and a second rod 220 (FIGS. 10-11). According to various embodiments disclosed herein, the implant 100 includes a connector body 110. Connector body 110 includes a first rod channel 1101 configured to receive a first rod 210, and a second rod channel 1102 configured to receive a second rod 220. The first rod channel 1101 may be substantially parallel to the second rod channel 1102, and the second rod channel 1102 may be laterally offset from first rod channel 1101 within connector body 110. First rod channel 1101 is further configured to open to an opposing side 1108 of the connector body 110 from the side 1109 to which second rod channel 1102 opens, such that first rod 210 enters first rod channel 1101 from the opposite side 1108 of connector body 110 from the side 1109 on which second rod 220 enters second rod channel 1102. The side 1108, to which first rod channel 1101 opens, may be considered the bottom of connector body 110, and the side 1109, to which second rod channel 1102 opens, may be considered the top of connector body 110.

Connector body 110 further includes a recess 1104 disposed therein. The recess 1104 may take the form of a hollowed out portion within connector body 110. The recess 1104 extends through the connector body 110 and spans the distance between the first rod channel 1101 and the second rod channel 1102. Recess 1104 thus opens at a proximal end to first rod channel 1101 and at the distal end thereof to second rod channel 1102. Recess 1104 may further be at least partially open to the same side 1108 of the connector body 110 as first rod channel 1101 (see, e.g., FIGS. 3, 8), e.g., to the bottom of the connector implant 100. In certain embodiments, recess 1104 may additionally be at least partially open to, i.e. include an opening 1111 (FIGS. 1-3) on the same side 1109 of the connector body 110 as second rod channel 1102. The side 1109 of connector body 110 to which second rod channel 1102 and recess 1104 open may be considered the top of the connector implant 100.

Connector implant 100 further includes a locking member 120 that is movably coupled to the connector body 110. Locking member 120 is disposed at least partially within the recess 1104 of connector body 110. Locking member 120 extends proximally into first rod channel 1101 and distally into second rod channel 1102. Locking member 120 may include a first rod locking surface 1203 that is configured to extend into the first rod channel 1101 in the locked position, to retain the first rod 210 in the first rod channel 1101. Locking member 120 may further include a retention feature 1205 disposed at the distal end of the second rod contact surface 1204. The interaction of retention feature 1205 with connector body 110 is described further herein.

Locking member 120 may be movably coupled to the connector body 110. FIG. 1 illustrates an embodiment in which connector body 110 may include a first bore 1103 passing through a thickness thereof. The first bore 1103 may pass through connector body 110 in a direction substantially perpendicular to the proximal/distal direction, and substantially parallel to the orientation of first rod channel 1101. First bore 1103 may further pass through a portion connector body 110 that is hollowed out to form recess 1104, such that the first bore 1103 passes through the walls of connector body 110 defining the recess 1104. Locking member 120 may include a second bore 1202 that passes through a thickness thereof. Like first bore 1103, second bore 1202 may pass through locking member 120 in a direction substantially perpendicular to the proximal/distal direction, and when installed, substantially parallel to first rod channel 1101. Second bore 1202 may be disposed in a head portion 1201 (FIG. 1) of locking member 120, about which the locking member moves or pivots in use. When locking member 120 is located within recess 1104, second bore 1202 is aligned with first bore 1103. A connection member 130 may then be disposed within first and second bores 1103, 1202, such that locking member 120 pivots around the connection member 130 to move or toggle between the unlocked position and the locked position. Connection member 130 may be, e.g., a pin.

In other embodiments, the connection between locking member 120 and connector body 110 may take a number of other forms. In one embodiment, connection member 130 may be integrally formed with locking member 120, in particular with head portion 1201 of locking member 120. In such an embodiment, recess 1104 within connector body 110 may be open to the top side 1109 of connector body 110, and the locking member 120 with integrally formed connection members may be seated into connector body 110 via the opening 1111 on the top side 1109 of the connector body 110, allowing the locking member 120 to rotate about the T-shaped integral connection member(s). In another embodiment, locking member 120 may be disposed within a track (not pictured) in connector body 110. In such an embodiment, the locking member 120 may translate in a proximal/distal direction along the track within connector body 110 rather than pivoting about a connection member 130. In still a further embodiment, the connector body 110 may include a compliant portion configured to flex into the first rod channel 1101 and into first rod 210 when pushed by the second rod 220 in second rod channel 1102.

Connector implant 110 further includes a fixation or closure member 140 for engaging a socket 1105. Socket 1105 is disposed at or near the opening of second rod channel 1102, and is configured to receive a fixation or closure member 140.

When the connector implant 100 is in an unlocked position (e.g., FIG. 2), the locking member 120 is positioned within recess 1104 in a manner that does not obstruct first rod channel 1101 or second rod channel 1102, and thus allows or enables the first rod 210 to be received within the first rod channel 1101, and the second rod 220 to be received within the second rod channel 1102.

When the connector implant 100 is in a locked position (FIGS. 4-5, 11), closure member 140 acts as a single locking mechanism for retaining the first rod 210 in the first rod channel 1101 and the second rod 220 in the second rod channel 1102. In certain embodiments, in the locked position, the closure member 140 engages the socket 1105 to retain the second rod 220 in the second rod channel 1102, held within second rod channel 1102 between closure member 140 and the second rod contact surface 1204. In this position, a force applied by the second rod 220 on the second rod contact surface 1204 of the locking member 120 acts to retain the position of locking member 120 in which the first rod 210 is retained within the first rod channel 1101. In some embodiments, socket 1105 may be in the form of a guide and advancement structure, and may more particularly be a helically wound flange feature. Closure member 140 may be in the form of a locking cap.

Figures 4, 5:
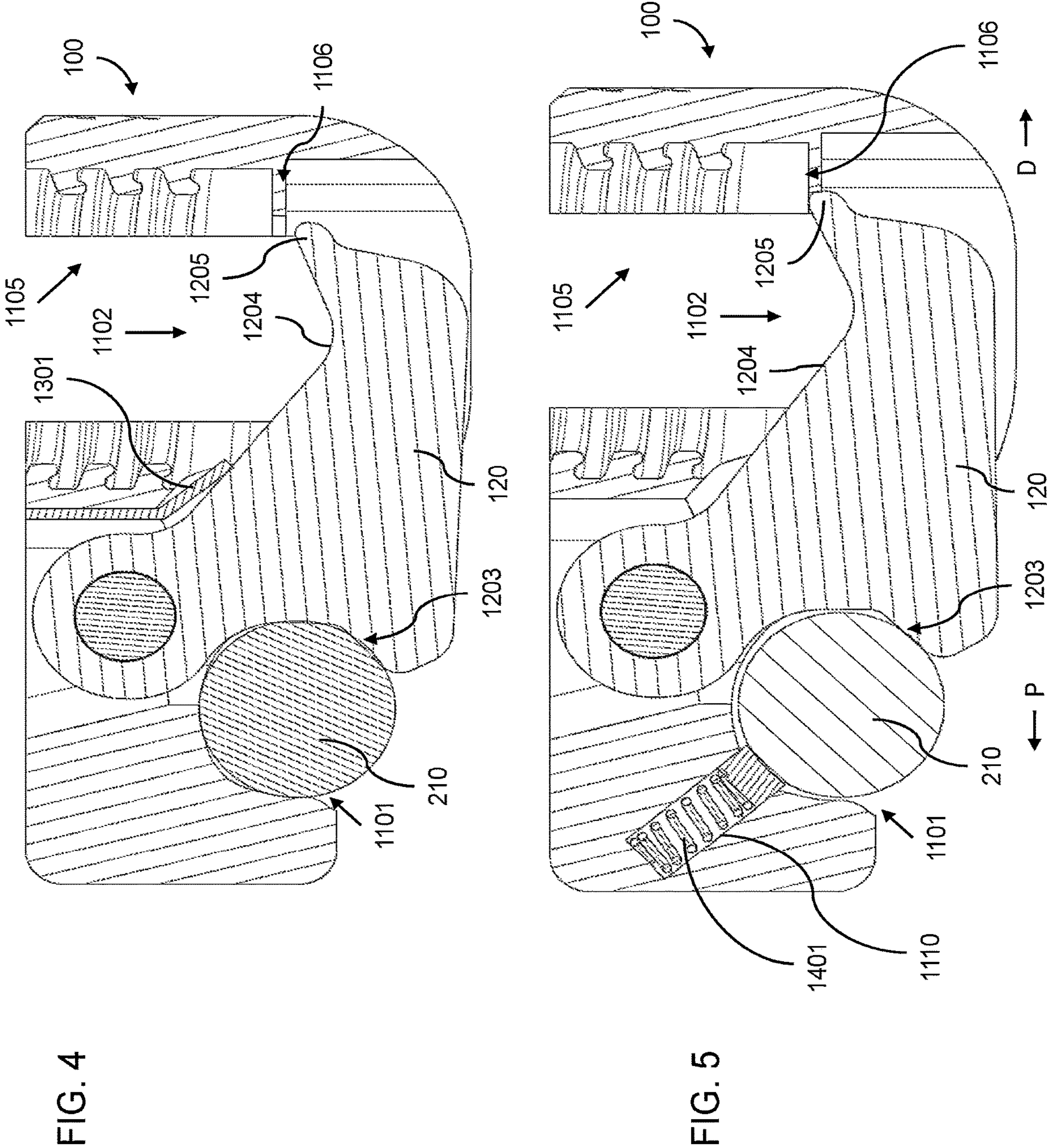
FIGS. 4-5 show side cross sectional views of a rod-to-rod connector implant and a first rod, according to embodiments of the invention.
Figure 6:
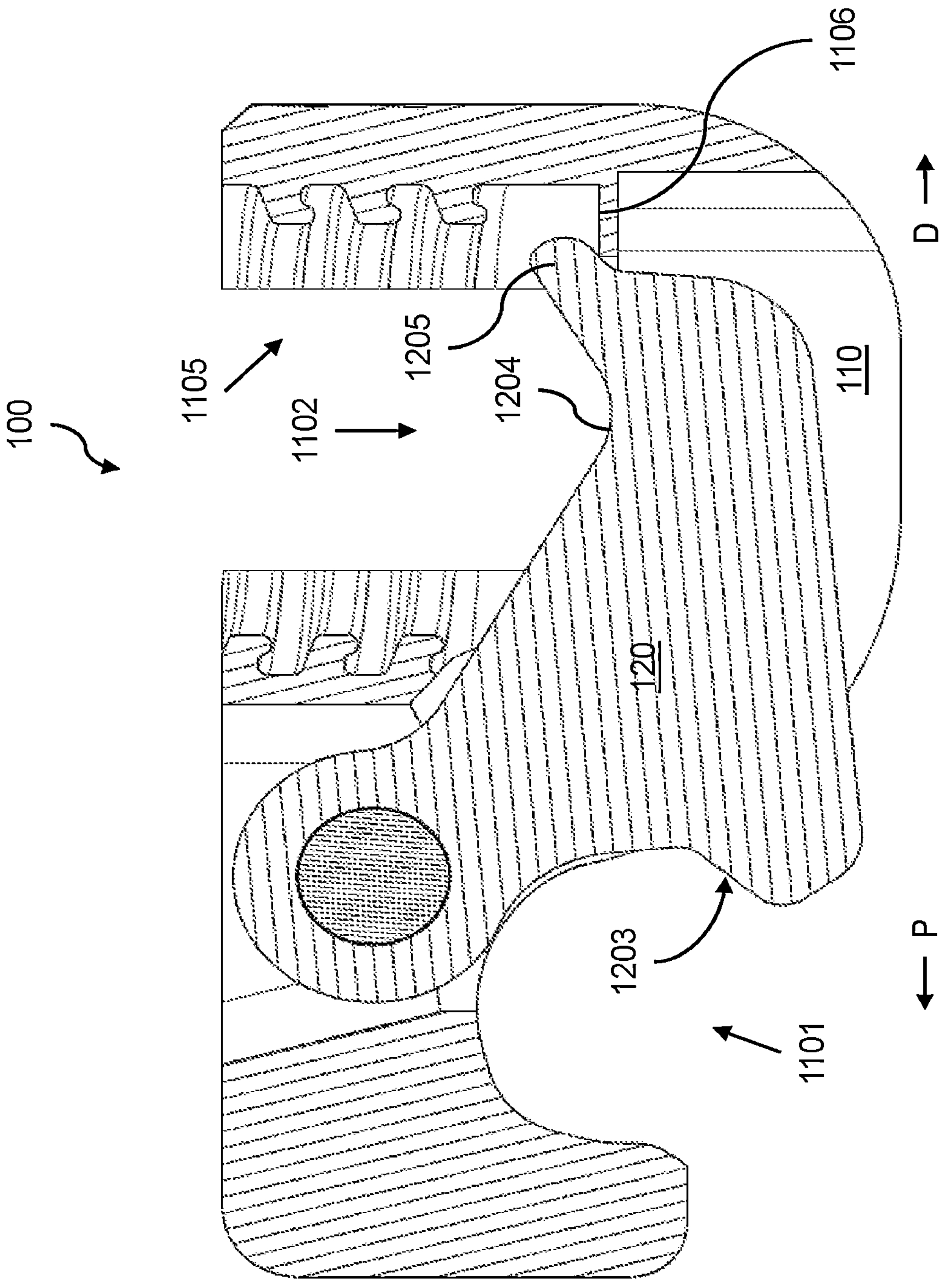
FIG. 6 shows a side cross sectional view of a portion of rod-to-rod connector implant including a locking member retention mechanism according to an embodiment of the invention.

With reference to FIG. 4, in one embodiment, a locking member biasing element 1301 is further provided. Locking member biasing element 1301 may be configured to bias the locking member 120 to move or pivot, e.g., about connection member 130, into first rod 210 with a constant force. Locking member biasing element 1301 may be, e.g., a leaf spring, that is configured to apply the force onto the locking member 120, rotating it towards first rod channel 1101 and first rod 210. The spring force applied by locking member biasing element 1301 may be sufficient to maintain a friction fit between first rod 210 and connector implant 100, e.g., between first rod locking surface 1203 of locking member 120, and first rod channel 1101 of connector body 110. The spring force applied by locking member biasing element 1301 may be configured to be overcome by the force of loading connector implant 100 onto first rod 210, i.e., insertion of first rod 210 into first rod channel 1101. Upon such loading force, the force applied by locking member biasing element 1301 would be overcome, and the locking member 120 would move or pivot, e.g., about connector member 130, at least partially out of first rod channel 1101. Once first rod 210 is located in first rod channel 1101, locking member 120 is configured to move, pivot, or snap back toward first rod 210 to provide a snug friction fit between first rod 210 and connector implant 100. As illustrated in FIG. 4, locking member biasing element 1301 is disposed adjacent to second rod channel 1102 and socket 1105, however, in other embodiments, locking member biasing element 1301 may be disposed in any location that allows a biasing force to be applied on locking member 120 toward first rod channel 1101.

With reference to FIG. 5, in another embodiment, a first rod biasing element 1401 is provided. First rod biasing element 1401 is configured to bias the first rod 210 into the locking member 120 with a constant force. First rod biasing element 1401 may be, e.g., a spring-loaded plunger disposed in a bore 1110 within connector body 110 that opens to first rod channel 1101. Bore 1110 may be disposed on a proximal side of first rod channel 1101, and may be substantially opposite first rod contacting surface 1203, such that when first rod 210 is fully seated in first rod channel 1101, first rod biasing element 1401 biases first rod 210 into first rod contacting surface 1203 of locking member 120. This arrangement is configured to prevent locking member 120 from moving or pivoting, e.g., about connection member 130, toward first rod 210 beyond a certain distance, thus wedging the first rod 210 between the first rod biasing element 1401 and the locking member 120.

In certain embodiments, a retention mechanism for locking member 120 may be provided. The retention mechanism may be configured to be overcome by the force applied by second rod 220 on locking member 120. For example, with respect to FIG. 6, connector body 110 may include a ledge or shoulder 1106, which may be disposed near or proximate to the bottom or deepest point of socket 1105 and second rod channel 1102. Locking member 120 may be provided with a corresponding retention feature 1205, which may take the form of, e.g., a nub, beam, or other protrusion configured to engage with shoulder 1106. In an unlocked position, retention feature 1205 of locking member 120 is configured to engage or rest on shoulder 1106. Shoulder 1106 may be configured to bend out of the way under force applied to locking member 120, urging locking member 120 to move or pivot, e.g., about connection member 130, toward and/or into first rod channel 1101. In various embodiments, shoulder 1106 may deform permanently, or may be sufficiently compliant to bend back after accommodating retention feature 1205 under force applied to locking member 120. Retention feature 1205, and its engagement with shoulder 1106, serve to retain the position of locking member 120, and prevent locking member 120 from moving or pivoting proximally toward or into first rod channel 1201 prematurely, which may have the effect of preventing insertion of first rod 210 into first rod channel 1101.

Figures 7, 8:
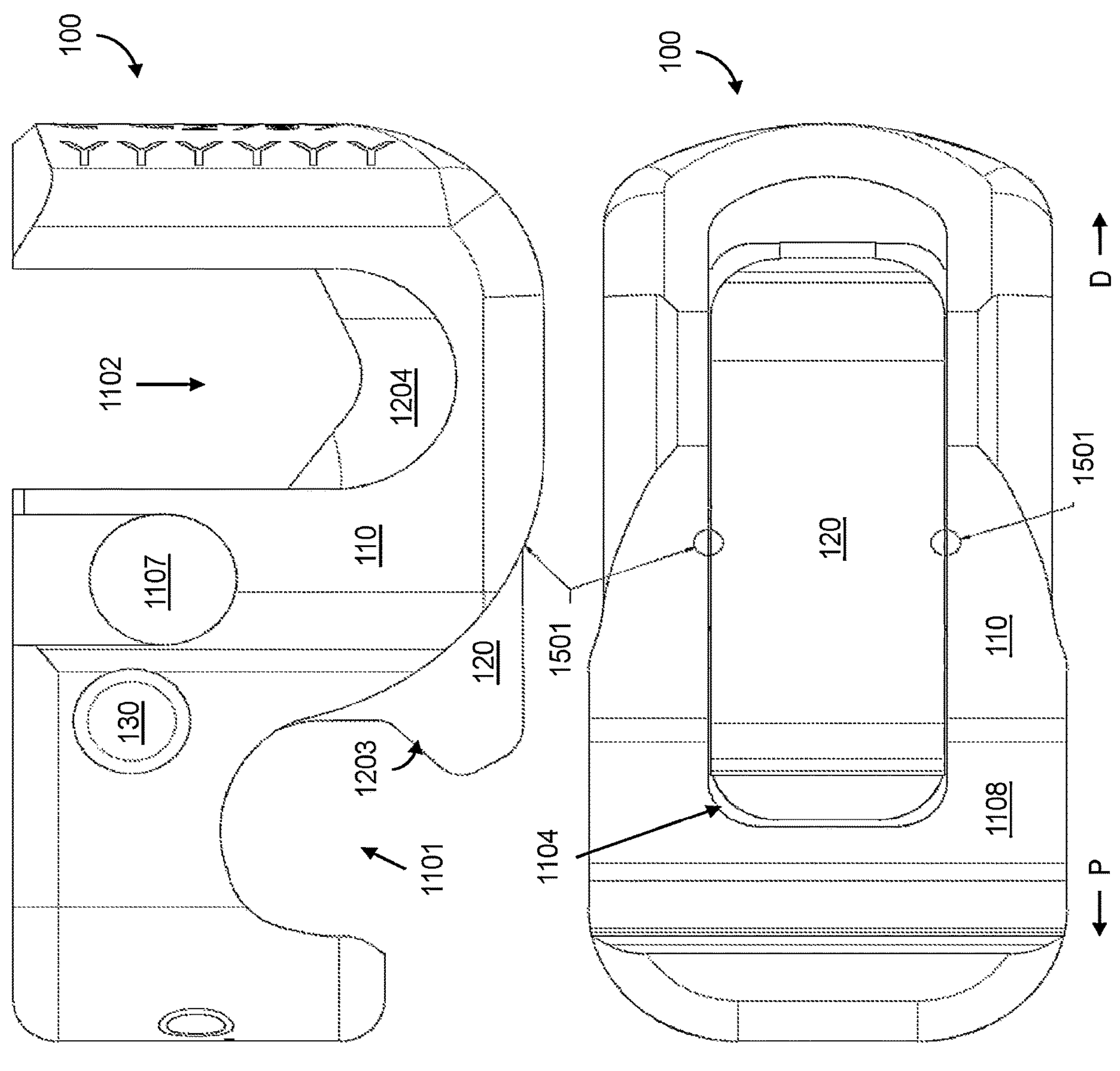
FIGS. 7 and 8 show a side view and a bottom view, respectively, of a portion of a rod-to-rod connector implant including a locking member retention mechanism according to an embodiment of the invention.

In another embodiment, shown in FIGS. 7-8, the locking member 120 retention mechanism may be provided in the form of a small weld 1501 between connector body 110 and locking member 120. Weld 1501 may be configured to break under the application of a force that exceeds a certain threshold. Thus, the weld 1501 may retain locking member 120 in the unlocked position until a threshold-exceeding force is applied on weld 1501 by the insertion of first rod 210 into first rod channel 1101 and pressing the connector body 110 downward onto first rod 210. In other embodiments, the threshold-exceeding force may be applied on weld 1501 by second rod 220 as it pushes on locking member 120.

In a further embodiment, a swaging process may be used to create a retention feature. With reference to FIG. 9, a blind drill hole 1601 may be provided on the distal outer surface of connector body 110. A punch tool may be used therein to deform the material of connector body 110, and push the material into the locking member 120 when held at a certain orientation. This process may be configured to create a wedge just proximal of blind drill hole 1601. The wedge would be pushed distally back into blind drill hole 1601 and out of the way of locking member 120 once enough force is applied to rotate the locking member 120.

In various embodiments, the connector body 110, the locking member 120, the connection member 130 if present, and the closure member 140 each include titanium in their composition.

Turning to FIGS. 10-11, as previously indicated, aspects of the invention provide a system 200 configured for use in orthopedic fixation applications, e.g., spinal fixation. The system 200 may include a first rod 210, a second rod 220; and a rod-to-rod connector implant 100 configured to couple the first rod 210 to the second rod 220.

Various embodiments of rod-to-rod connector implants are described herein with respect to FIGS. 1-9. System 200 is understood to include a connector implant 100 in accordance with any embodiments described herein, which may be used to couple first rod 210 to second rod 220.

Each of first rod 210 and second rod 220 may have a circular cross sectional shape, and may further have an outer diameter which may vary with the specific application. For example, each of first rod 210 and second rod 220 may have an outer diameter of about 3.5 mm to about 4.0 mm. Such dimensions may be suitable for, e.g., cervical spine applications. However, in other embodiments, first rod 210 and second rod 220 may have other dimensions. For example, first rod 210 and second rod 220 may each have an outer diameter larger than about 3.5 mm to about 4.0 mm, for use in, e.g., thoracolumbar applications, as is known in the art. Regardless of the specific dimensions, each of first rod channel 1101 and second rod channel 1102 may be configured to accept more than one diameter rod 210, 220 within the slot. For example, each rod channel 1101, 1102 may be configured to accept either of, e.g., a 3.5 mm or 4.0 mm rod. Additionally, first rod 210 need not have the same outer diameter as second rod 220, and vice versa. First and second rods 210, 220 may further comprise a metallic material such as, e.g., titanium, titanium alloy, stainless steel, and so on, as known in the art.

In certain embodiments, connector implant 100 may be used as part of a system 200 for use in a surgical revision procedure. In such embodiments, the first rod 210 is an index rod, which is part of a pre-existing construct, while the second rod 220 is an extension rod. Connector implant 100 may be loaded onto the existing index rod 210 to couple the index rod 210 to a second, extension rod 220 to build onto an existing construct without requiring surgical removal of existing components. In other embodiments, connector implant 100 may be used as part of a system 200 for use in a primary surgical procedure. In such embodiments, both first rod 210 and second rod 220 are extension rods, or new rods. Connector implant 100 may be loaded onto first rod 210 after its insertion, and second rod 220 may subsequently be inserted into second rod channel 1102 and secured.

As previously indicated, aspects of the invention provide a method of inserting a rod-to-rod connector implant 100, e.g., in spinal fixation procedure applications. According to various embodiments, the method may include the following steps:

a) Providing a rod-to-rod connector implant 100 having a connector body 110, a locking member 120, a fixation member 140, and other features depending on the particular embodiment, as described herein with reference to any of FIGS. 1-9, and/or as illustrated in any of FIGS. 1-9.

b) Using forceps 150 (FIGS. 12-13), inserting or loading the connector implant 100, and particularly connector body 110, onto the first rod 210, such that the first rod 210 is disposed within the first rod channel 1101 as shown in FIGS. 10-11. This step may include inserting the connector body 110 downward onto the first rod 210, wherein the first rod channel 1101 opens to a bottom surface of the connector body 110. The first rod 210 may already be fixed in position in a patient, and may either be an index rod or an extension rod depending on the nature of the procedure as previously described.

c) Inserting the second rod 220 into the second rod channel 1102 of the connector body 110 from the opposing side of the connector body 110. Second rod 220 may be an extension rod, as previously described. Second rod 220 may be inserted downward into the second rod channel 1102, wherein the second rod channel 1102 is open to a top surface of the connector body 110.

d) Contacting, with the second rod 220, a second rod contact surface 1204 of the locking member 120, and actuating movement of the locking member 120 at least partially out of second rod channel 1102. This movement causes first rod locking surface 1203 to extend into the first rod channel 1101, thereby retaining first rod 210 within first rod channel 1101.

e) Inserting a closure member 140 into the socket 1105 in second rod channel 1102 to lock the rod-to-rod connector implant 100 onto the first and the second rods 210, 220 with a single locking mechanism. Closure member 140 may be inserted downward into the socket 1105, and the socket 1105 may be disposed at the opening of the second rod channel 1102 at the top surface of the connector body 110.

Depending on the embodiment, additional steps may be performed to accommodate features described in greater detail above with respect to the connector implant 100. For example, where the instant method commences with the provision of a connector implant 100 including a first rod biasing element 1401 as depicted in FIG. 5, between step a) and step b), in certain embodiments, first rod biasing element 1401 may be inserted into bore 1110, or the presence of first road biasing element 1401 within bore 1110 may be confirmed prior to loading connector implant 100 onto first rod 210. In another example, where the instant method commences with the provision of a connector implant 100 including a retention mechanism as depicted in FIG. 9, the swaging process described herein may be performed prior to step b).

Figures 12, 13:
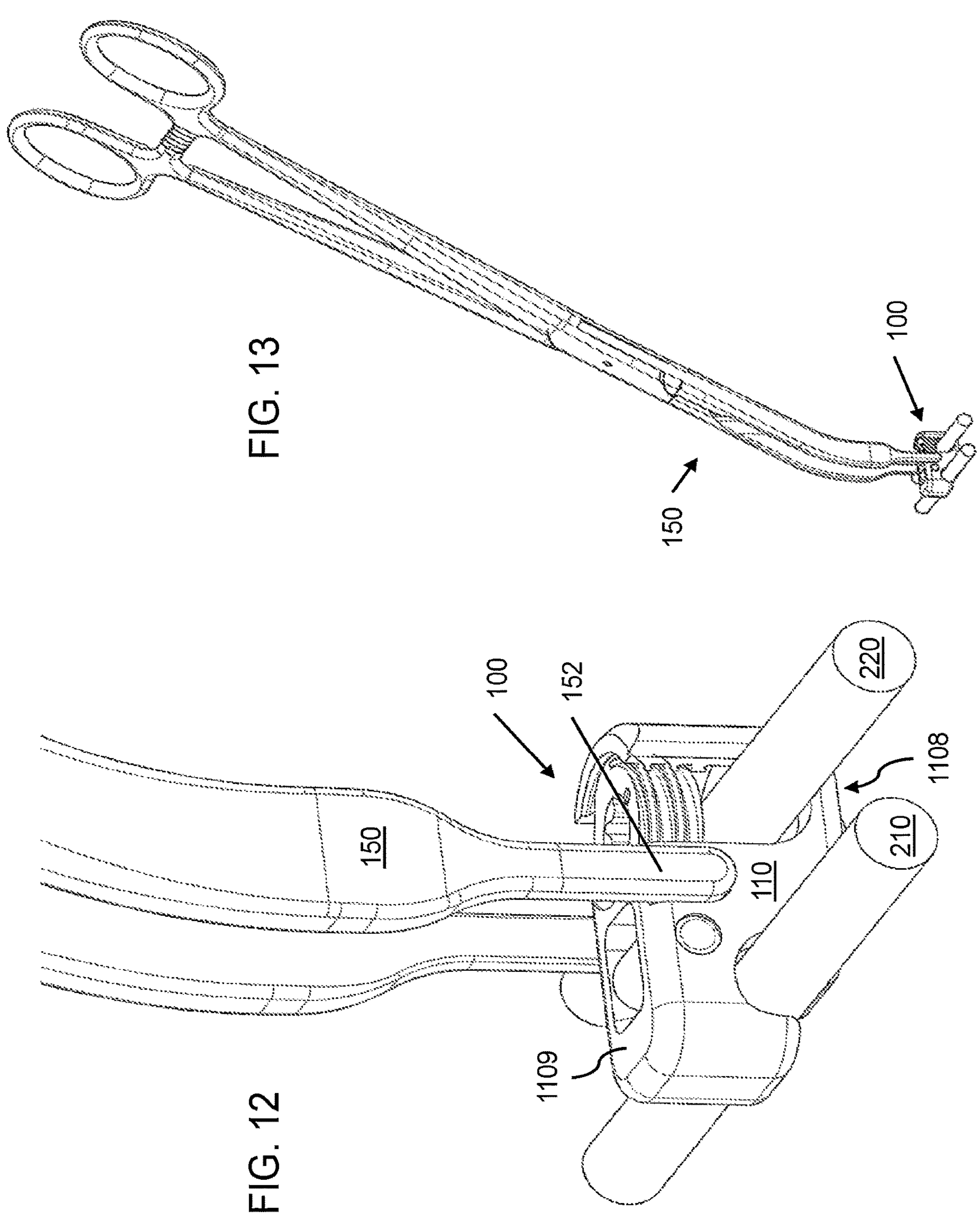
FIGS. 12 and 13 show perspective views of kit components, including a rod-to-rod connector implant and forceps for insertion of the same, according to embodiments of the invention.

Turning to FIGS. 12-13, as previously indicated, aspects of the invention provide a kit for use in spinal fixation applications. The kit may include a rod-to-rod connector implant 100 and a pair of forceps 150 configured for use inserting the rod-to-rod connector implant into a patient as described above.

Various embodiments of rod-to-rod connector implants are described herein with respect to FIGS. 1-9. The kit disclosed herein is understood to include a connector implant 100 in accordance with any embodiments described or depicted herein.

As provided in the kit disclosed herein, the rod-to-rod connector implant 100 includes a connector body 110 having a first rod channel 1101 and a second rod channel 1102, wherein the first rod channel 1101 opens to an opposing side of the connector body from the second rod channel 1102. The first rod channel 1101 is laterally offset from the second rod channel 1102 as described herein. The first rod channel 1101 may be open to a bottom surface of the connector body 110, while the second rod channel 1102 may be open to a top surface of the connector body 110. The first rod channel 1101 is arranged to be substantially parallel to the second rod channel 1102. A recess 1104 is provided spanning between the first rod channel 1101 and the second rod channel 1102 through the connector body. The recess 1104 may be open to the bottom surface of the connector body, and to the second rod channel 1102 at a bottom thereof.

Connector implant 100 as provided in the kit further includes a locking member 120 movably coupled to the connector body 110. As previously described, the locking member 120 is located at least partially within the recess 1104 and extends into the first rod channel 1101 and the second rod channel 1102. The locking member 120 may further comprise a first rod locking surface 1203 configured to extend into the first rod channel 1101 in the locked position, to retain the first rod 210 in the first rod channel 1101. The locking member 120 is movably coupled to connector body 110, and in certain embodiments, may be pivotably coupled thereto.

In certain embodiments, a first bore 1103 may be disposed through a thickness of the connector body 110. The first bore 1103 may particularly pass through a portion of the recess 1104 and sidewalls of connector body 110 that define the recess 1104. A second bore 1202 may be disposed through a head portion 1201 thickness of the locking member 120. First and second bores 1103, 1202 may be aligned with one another. A connection member 130 may be disposed within the first and second bores 1103, 1202, such that the locking member 120 pivots around the connection member 130 to move or toggle between an unlocked position and the locked position. As described previously herein, however, other means of moveably coupling connector body 110 to locking member 120 described elsewhere herein are equally considered part of the invention.

A closure member 140 is provided for engaging a socket 1105 in the second rod channel 1102. The socket 1105 may be a guide and advancement structure, and may more particularly be a helically wound flange feature. The closure member 140 may particularly be a locking cap.

In a locked position, the closure member 140 acts as a single locking mechanism for retaining the first rod 210 in the first rod channel 1101 and the second rod 220 in the second rod channel 1102. In particular, the closure member 140 may engage the socket 1105 to retain the second rod 220 in the second rod channel 1102. A force applied by the second rod 220 to a second rod contact surface 1204 of the locking member 120 further retains the first rod 210 in the first rod channel 1101.

In an unlocked position, the locking member 120 may enable the first rod to be received in the first rod channel 1101 and the second rod 220 to be received in the second rod channel 1102.

In certain embodiments, connector implant 100 includes a retention mechanism. In particular, as previously described with respect to FIG. 6, the locking member 120 may include a retention feature 1205 disposed at a distal end of the second rod contact surface 1204, and connector body 110 may further comprises a shoulder 1106 configured to engage with the retention feature 1205 in the unlocked position. A connector implant 100 including a retention mechanism as described above with respect to any of FIGS. 6-8 may also be provided in the context of the kit.

The connector body may further include a pair of indentations 1107 (FIGS. 1-3, 7, and 10-11). The forceps 150 include a tip 152 (FIG. 12) that has a complementary fit with the pair of indentations 1107; i.e., indentations 1107 have a shape and a size configured to matingly engage with a tip of the forceps 150 (FIGS. 12-13).

In various embodiments, the connector body 110, the locking member 120, the connection member 130 if present, and the closure member 140 each include titanium in their composition.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A rod-to-rod connector implant for joining a first rod and a second rod, the implant comprising:
- a connector body including:
  - a first rod channel and a second rod channel, wherein the first rod channel opens to a lower side of the connector body and the second rod channel opens to an upper side opposite the lower side of the connector body, such that a first rod enters the first rod channel from the lower side and a second rod enters the second rod channel from the upper side, and wherein the first rod channel is laterally offset from the second rod channel; and
  - a recess spanning between the first rod channel and the second rod channel through the connector body;
- a locking member pivotably coupled to the connector body via a pin, the pin located closer to the upper side of the connector body than the lower side of the connector body, the locking member being located at least partially within the recess and extending into the first rod channel and the second rod channel, wherein the second rod channel is configured to receive the second rod such that the second rod is seated on a contact surface of the locking member; and
- a closure member configured to be inserted from the upper side to engage a socket in the second rod channel, wherein in a locked position, the closure member acts as a single locking mechanism for retaining the first rod in the first rod channel and the second rod in the second rod channel.

2. The rod-to-rod connector implant of claim 1, wherein in an unlocked position, the locking member enables the first rod to be received in the first rod channel and the second rod to be received in the second rod channel.

3. The rod-to-rod connector implant of claim 2, wherein in the locked position, the closure member engages the socket to retain the second rod in the second rod channel, and a force applied by the second rod to the contact surface of the locking member retains the first rod in the first rod channel.

4. The rod-to-rod connector implant of claim 3, wherein the locking member further comprises a first rod locking surface configured to extend into the first rod channel in the locked position, to retain the first rod in the first rod channel.

5. The rod-to-rod connector implant of claim 3, wherein the locking member further comprises a retention feature disposed at a distal end of the second rod contact surface, and the body further comprises a shoulder disposed proximate to a bottom of the socket, the shoulder being configured to engage with the retention feature in the unlocked position.

6. The rod-to-rod connector implant of claim 1, wherein the locking member is pivotably coupled to the connector body.

7. The rod-to-rod connector implant of claim 6, further comprising:

- a first bore through a thickness of the connector body, and passing through a portion of the recess;
- a second bore through a thickness of the locking member and aligned with the first bore; and
- a connection member disposed within the first and second bores, such that the locking member pivots around the connection member to move between an unlocked position and the locked position.

8. The rod-to-rod connector implant of claim 1, wherein the first rod channel is open to a bottom surface of the connector body, the second rod channel is open to a top surface of the connector body, and the first rod channel is substantially parallel to the second rod channel.

9. The rod-to-rod connector implant of claim 8, wherein the recess is open to the bottom surface of the connector body, and to the second rod channel at a bottom thereof.

10. The rod-to-rod connector implant of claim 1, wherein the socket is a guide and advancement structure, and the closure member a locking cap.

11. The rod-to-rod connector implant of claim 10, wherein the guide and advancement structure is a helically wound flange feature.

12. The rod-to-rod connector implant of claim 1, wherein the connector body, the locking member, the connection member, and the closure member each include titanium.

13. A system comprising:

- a first rod;
- a second rod; and
- a rod-to-rod connector implant coupling the first rod to the second rod, the connector implant comprising:
  - a connector body including:
    - a first rod channel and a second rod channel, wherein the first rod channel opens to a lower side of the connector body and the second rod channel opens to an upper side opposite the lower side of the connector body, such that the first rod enters the first rod channel from the lower side and the second rod enters the second rod channel from the upper side, and wherein the first rod channel is laterally offset from the second rod channel; and
    - a recess spanning between the first rod channel and the second rod channel through the connector body;
  - a locking member pivotably coupled to the connector body via a pin, the pin located closer to the upper side of the connector body than the lower side of the connector body, the locking member being located at least partially within the recess and extending into the first rod channel and the second rod channel, wherein the second rod channel is configured to receive a second rod such that the second rod is seated on a contact surface of the locking member; and
  - a closure member configured to be inserted from the upper side to engage a socket in the second rod channel,
- wherein in a locked position, the closure member acts as a single locking mechanism for retaining the first rod in the first rod channel and the second rod in the second rod channel.

14. The system of claim 13, wherein the first rod is an index rod, and the second rod is an extension rod.

15. The system of claim 13, wherein the first rod is a first extension rod, and the second rod is a second extension rod.

16. The system of claim 13, wherein the first rod and the second rod each have a circular cross section, and an outer diameter of 3.5 mm to 4.0 mm.

17. A method of inserting a rod-to-rod connector implant, comprising:

- providing a rod-to-rod connector implant including:
  - a connector body having a first rod channel and a second rod channel, wherein the first rod channel opens to a lower side of the connector body and the second rod channel opens to an upper side opposite the lower side of the connector body, such that a first rod enters the first rod channel from the lower side and a second rod enters the second rod channel from the upper side, and wherein the first rod channel is laterally offset from the second rod channel; and
  - a recess spanning between the first rod channel and the second rod channel through the connector body;
  - a locking member pivotably coupled to the connector body, the locking member being located at least partially within the recess and extending into the first rod channel and the second rod channel; and
  - a closure member for engaging a socket in the second rod channel;
- using forceps, inserting the connector body onto a first rod such that the first rod is disposed within the first rod channel, wherein the first rod is fixed in position in a patient,
- inserting a second rod into the second rod channel from the opposing side of the connector body,
- with the second rod, contacting a second rod contact surface of the locking member, and actuating movement of the locking member at least partially out of the second rod channel such that the first rod locking surface extends into the first rod channel, thereby retaining the first rod within the first rod channel; and
- inserting the closure member through the upper side and into the socket to lock the rod-to-rod connector implant onto the first and the second rods, with a single locking mechanism.

18. The method of claim 17, wherein the first rod is an index rod, and the second rod is an extension rod.

19. The method of claim 17, wherein the first rod is a first extension rod, and the second rod is a second extension rod.

20. The method of claim 17, further comprising:

inserting the connector body downward onto the first rod, wherein the first rod channel opens to a bottom surface of the connector body;

inserting the second rod downward into the second rod channel, wherein the second rod channel is open to a top surface of the connector body; and inserting the closure member downward into the socket, wherein the socket is disposed at the opening of the second rod channel at the top surface of the connector body.

* * * * *